(12) United States Patent
Atkin et al.

(10) Patent No.: US 12,208,021 B2
(45) Date of Patent: Jan. 28, 2025

(54) PROSTHESIS EXTRACTION SYSTEM

(71) Applicant: DEPUY IRELAND UNLIMITED COMPANY, Ringaskiddy (IE)

(72) Inventors: Jamie Atkin, Sheffield (GB); Graeme Dutton, Burnley (GB); Gary Moore, Leeds (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 855 days.

(21) Appl. No.: 17/282,017

(22) PCT Filed: Oct. 3, 2019

(86) PCT No.: PCT/EP2019/076812
§ 371 (c)(1),
(2) Date: Apr. 1, 2021

(87) PCT Pub. No.: WO2020/070244
PCT Pub. Date: Apr. 9, 2020

(65) Prior Publication Data
US 2021/0353430 A1 Nov. 18, 2021

(30) Foreign Application Priority Data
Oct. 4, 2018 (GB) ...................................... 1816197

(51) Int. Cl.
*A61F 2/46* (2006.01)
(52) U.S. Cl.
CPC .......... *A61F 2/4603* (2013.01); *A61F 2/4607* (2013.01); *A61F 2002/4619* (2013.01);
(Continued)
(58) Field of Classification Search
CPC ................... A61F 2/4603; A61F 2/4607; A61F 2002/4619; A61F 2002/4627;
(Continued)

(56) References Cited

U.S. PATENT DOCUMENTS 3,801,989 A 4/1974 McKee
3,818,514 A 6/1974 Clark
(Continued)

FOREIGN PATENT DOCUMENTS

AU 617009 B2 11/1991
AU 2002246466 A1 10/2002
(Continued)

OTHER PUBLICATIONS

US 9,445,923 B2, 09/2016, Aghazadeh (withdrawn)
(Continued)

*Primary Examiner* — Sarah W Aleman
(74) *Attorney, Agent, or Firm* — Barnes & Thornburg LLP

(57) ABSTRACT

A surgical device (2) for extraction of a prosthetic component from a patient during surgery. The surgical device comprises a first component (8) having a female coupling portion at a first end, and a second end configured to be connected to one of a prosthetic component or a surgical extraction instrument. The first component further includes a retainer. The surgical device further comprises a second component (10) with a first end defining a male coupling portion, a stem (30, 130) extending from the male coupling portion, and a second end configured to be connected to the other of the prosthetic component or the surgical extraction instrument. The male coupling portion of the second component is configured to be disposed within the female coupling portion of the first component and retained within the female coupling portion by the retainer, with the stem of the second component extending away from the female coupling portion of the first component. The male coupling portion of the second component and the retainer of the first component are configured such that the male coupling portion is held in the female coupling portion while allowing (Continued)

articulation of the first component relative to the second component. The first and second components form an articulating joint allowing a user to connect the surgical extraction instrument to the prosthetic component in a patient, articulate a portion of the surgical extraction instrument which resides external from the operating site, and transfer extraction forces to enable removal of the prosthetic component from the patient.

11 Claims, 20 Drawing Sheets

(52) U.S. Cl.
  CPC .............. *A61F 2002/4627* (2013.01); *A61F 2002/4629* (2013.01)

(58) Field of Classification Search
  CPC ...... A61F 2002/4629; A61F 2002/4625; A61F 2002/4681
  See application file for complete search history.

(56) References Cited

U.S. PATENT DOCUMENTS

| | | | |
|---|---|---|---|
| 3,874,003 A | 4/1975 | Moser et al. |
| 3,955,568 A | 5/1976 | Neufeld |
| 4,222,382 A | 9/1980 | Antonsson et al. |
| 4,310,931 A | 1/1982 | Mueller |
| 4,502,160 A | 3/1985 | Moore et al. |
| 4,514,865 A | 5/1985 | Harris |
| 4,530,114 A | 7/1985 | Tepic |
| 4,536,894 A | 8/1985 | Galante et al. |
| 4,551,863 A | 11/1985 | Murray |
| 4,601,289 A | 7/1986 | Chiarizzio et al. |
| 4,605,416 A | 8/1986 | Grobbelaar |
| 4,624,673 A | 11/1986 | Meyer |
| 4,642,121 A | 2/1987 | Keller |
| 4,661,112 A | 4/1987 | Mueller |
| 4,686,971 A | 8/1987 | Harris et al. |
| 4,714,470 A | 12/1987 | Webb et al. |
| 4,728,334 A | 3/1988 | Spotorno |
| 4,728,335 A | 3/1988 | Jurgutis |
| 4,772,203 A | 9/1988 | Scheunemann |
| 4,792,339 A | 12/1988 | Tepic |
| 4,813,962 A | 3/1989 | Deckner et al. |
| 4,828,566 A | 5/1989 | Griss |
| 4,851,007 A | 7/1989 | Gray |
| 4,865,608 A | 9/1989 | Brooker, Jr. |
| 4,904,267 A | 2/1990 | Bruce et al. |
| 4,904,269 A | 2/1990 | Elloy et al. |
| 4,919,679 A | 4/1990 | Averill et al. |
| 4,921,500 A | 5/1990 | Averill et al. |
| 4,922,898 A | 5/1990 | Dunn |
| 4,936,863 A | 6/1990 | Hofmann |
| 4,946,461 A | 8/1990 | Fischer |
| 4,993,410 A | 2/1991 | Kimsey |
| 5,015,256 A | 5/1991 | Bruce et al. |
| 5,032,134 A | 7/1991 | Lindwer |
| 5,133,769 A | 7/1992 | Wagner et al. |
| 5,156,626 A | 10/1992 | Broderick et al. |
| 5,156,627 A | 10/1992 | Amstutz et al. |
| 5,163,961 A | 11/1992 | Harwin |
| 5,171,288 A | 12/1992 | Mikhail et al. |
| 5,171,324 A | 12/1992 | Campana et al. |
| 5,196,018 A | 3/1993 | Willert et al. |
| 5,222,958 A | 6/1993 | Chin |
| 5,258,034 A | 11/1993 | Furlong et al. |
| 5,282,805 A | 2/1994 | Richelsoph et al. |
| 5,290,318 A | 3/1994 | Ling et al. |
| 5,314,489 A | 5/1994 | Hoffman et al. |
| 5,314,493 A | 5/1994 | Mikhail |
| 5,342,362 A | 8/1994 | Kenyon et al. |
| 5,342,366 A | 8/1994 | Whiteside et al. |
| 5,343,877 A | 9/1994 | Park |
| 5,370,706 A | 12/1994 | Bolesky et al. |
| 5,405,404 A | 4/1995 | Gardner et al. |
| 5,443,523 A | 8/1995 | Mikhail |
| 5,456,686 A | 10/1995 | Klapper et al. |
| 5,456,717 A | 10/1995 | Zweymueller et al. |
| 5,468,245 A | 11/1995 | Vargas, III |
| 5,470,336 A | 11/1995 | Ling et al. |
| 5,476,466 A | 12/1995 | Barrette et al. |
| 5,514,136 A | 5/1996 | Richelsoph |
| 5,534,006 A | 7/1996 | Szabo et al. |
| 5,536,272 A | 7/1996 | Young et al. |
| 5,549,702 A | 8/1996 | Ries et al. |
| 5,601,567 A | 2/1997 | Swajger et al. |
| 5,665,121 A | 9/1997 | Gie et al. |
| 5,674,225 A | 10/1997 | Mueller |
| 5,702,480 A | 12/1997 | Kropf et al. |
| 5,735,857 A | 4/1998 | Lane |
| 5,743,910 A | 4/1998 | Bays et al. |
| 5,755,805 A | 5/1998 | Whiteside |
| 5,755,811 A | 5/1998 | Tanamal et al. |
| 5,769,092 A | 6/1998 | Williamson, Jr. |
| 5,788,704 A | 8/1998 | Timperley |
| 5,792,143 A | 8/1998 | Samuelson et al. |
| 5,849,015 A | 12/1998 | Haywood et al. |
| 5,858,020 A | 1/1999 | Johnson et al. |
| 5,885,295 A | 3/1999 | Mcdaniel et al. |
| 5,885,301 A | 3/1999 | Young |
| 5,888,245 A | 3/1999 | Meulink et al. |
| 5,989,259 A | 11/1999 | Penenberg et al. |
| 6,034,295 A | 3/2000 | Rehberg et al. |
| 6,110,179 A | 8/2000 | Flivik et al. |
| 6,113,605 A | 9/2000 | Storer |
| 6,126,691 A | 10/2000 | Kasra et al. |
| 6,165,177 A | 12/2000 | Wilson et al. |
| 6,179,877 B1 | 1/2001 | Burke |
| 6,187,012 B1 | 2/2001 | Masini |
| 6,190,416 B1 | 2/2001 | Choteau et al. |
| 6,193,759 B1 | 2/2001 | Ro et al. |
| 6,213,775 B1 | 4/2001 | Reipur |
| 6,217,583 B1 | 4/2001 | Storer |
| 6,228,120 B1 | 5/2001 | Leonard et al. |
| 6,245,111 B1 | 6/2001 | Shaffner |
| 6,287,342 B1 | 9/2001 | Copf et al. |
| 6,309,395 B1 | 10/2001 | Smith et al. |
| 6,336,941 B1 | 1/2002 | Subba Rao et al. |
| 6,347,564 B1 | 2/2002 | Ciocca |
| 6,371,991 B1 | 4/2002 | Manasas et al. |
| 6,375,684 B1 | 4/2002 | Kriek |
| 6,482,237 B2 | 11/2002 | Mosseri |
| 6,652,590 B1 | 11/2003 | Zitnansky et al. |
| 6,706,073 B2 | 3/2004 | Draenert et al. |
| 6,723,130 B2 | 4/2004 | Draenert et al. |
| 6,740,120 B1 | 5/2004 | Grimes |
| 6,746,487 B2 | 6/2004 | Scifert et al. |
| 6,749,637 B1 | 6/2004 | Bhler |
| 6,764,492 B2 | 7/2004 | Taft |
| 6,790,211 B1 | 9/2004 | Mcpherson et al. |
| 6,790,234 B1 | 9/2004 | Frankle |
| 6,840,942 B2 | 1/2005 | Storer et al. |
| 6,863,690 B2 | 3/2005 | Ball et al. |
| 6,884,264 B2 | 4/2005 | Spiegelberg et al. |
| 6,905,502 B2 | 6/2005 | Penenberg |
| 6,981,991 B2 | 1/2006 | Ferree |
| 6,984,248 B2 | 1/2006 | Hyde, Jr. |
| 6,988,009 B2 | 1/2006 | Grimm et al. |
| 6,991,655 B2 | 1/2006 | Iversen |
| 6,994,731 B2 | 2/2006 | Howie |
| 7,001,393 B2 | 2/2006 | Schwenke et al. |
| 7,004,972 B2 | 2/2006 | Yoon |
| 7,037,311 B2 | 5/2006 | Parkinson et al. |
| 7,122,056 B2 | 10/2006 | Dwyer et al. |
| 7,156,852 B2 | 1/2007 | Dye et al. |
| 7,179,259 B1 | 2/2007 | Gibbs |
| 7,229,478 B2 | 6/2007 | Masini |
| 7,238,207 B2 | 7/2007 | Blatter et al. |
| 7,244,273 B2 | 7/2007 | Pedersen et al. |
| 7,261,741 B2 | 8/2007 | Weissman et al. |
| 7,328,131 B2 | 2/2008 | Donofrio et al. |

(56) References Cited

U.S. PATENT DOCUMENTS

| | | |
|---|---|---|
| 7,468,075 B2 | 12/2008 | Lang et al. |
| 7,547,328 B2 | 6/2009 | Sidebotham |
| 7,572,297 B2 | 8/2009 | Cheal et al. |
| 7,611,513 B2 | 11/2009 | Delog et al. |
| 7,621,962 B2 | 11/2009 | Lakin |
| 7,695,474 B2 | 4/2010 | Crofford |
| 7,708,739 B2 | 5/2010 | Kilburn et al. |
| 7,766,968 B2 | 8/2010 | Sweeney |
| 7,828,805 B2 | 11/2010 | Hoag et al. |
| 7,828,851 B2 | 11/2010 | Mccleary et al. |
| 7,833,275 B2 | 11/2010 | Mears et al. |
| 7,875,083 B2 | 1/2011 | Sudmann |
| 7,927,338 B2 | 4/2011 | Laffargue et al. |
| 7,976,545 B2 | 7/2011 | Hershberger et al. |
| 7,993,566 B2 | 8/2011 | Pedersen et al. |
| 7,998,147 B2 | 8/2011 | Santarella et al. |
| 8,002,838 B2 | 8/2011 | Klotz |
| 8,066,775 B2 | 11/2011 | Branovacki |
| 8,078,254 B2 | 12/2011 | Murphy |
| 8,105,327 B2 | 1/2012 | Long et al. |
| 8,137,358 B2 | 3/2012 | Winslow et al. |
| 8,152,855 B2 | 4/2012 | Tulkis et al. |
| 8,162,947 B2 | 4/2012 | Dreyfuss |
| 8,252,062 B2 | 8/2012 | Bandoh et al. |
| 8,262,668 B2 | 9/2012 | Biegun |
| 8,277,457 B1 | 10/2012 | Burgi et al. |
| 8,282,649 B2 | 10/2012 | Long et al. |
| 8,292,895 B2 | 10/2012 | Bubb |
| 8,337,504 B2 | 12/2012 | Surma |
| 8,343,218 B2 | 1/2013 | Lang et al. |
| 8,361,162 B2 | 1/2013 | Berry et al. |
| 8,372,077 B2 | 2/2013 | Taylor |
| 8,398,719 B2 | 3/2013 | Walter et al. |
| 8,439,978 B2 | 5/2013 | Ebbitt |
| 8,469,962 B1 | 6/2013 | Head |
| 8,500,743 B2 | 8/2013 | Birkbeck et al. |
| 8,500,815 B2 | 8/2013 | Fockens |
| 8,529,572 B2 | 9/2013 | Nevels et al. |
| 8,545,504 B2 | 10/2013 | Durand-Allen et al. |
| 8,597,361 B2 | 12/2013 | Sidebotham et al. |
| 8,603,100 B2 | 12/2013 | Muller |
| 8,632,601 B2 | 1/2014 | Howald et al. |
| 8,657,833 B2 | 2/2014 | Burgi et al. |
| 8,690,880 B2 | 4/2014 | Bastian et al. |
| 8,696,758 B2 | 4/2014 | Hood et al. |
| 8,758,446 B2 | 6/2014 | Smith |
| 8,778,029 B2 | 7/2014 | Baumgart |
| 8,795,281 B2 | 8/2014 | Faccioli |
| 8,801,722 B2 | 8/2014 | Aeschlimann et al. |
| 8,814,946 B2 | 8/2014 | Steinberg |
| 8,845,650 B2 | 9/2014 | Imhof-Rthlin et al. |
| 8,876,909 B2 | 11/2014 | Meridew et al. |
| 8,900,245 B2 | 12/2014 | Splieth et al. |
| 8,926,627 B2 | 1/2015 | Iannotti et al. |
| 8,945,131 B2 | 2/2015 | Vanasse et al. |
| 8,961,614 B2 | 2/2015 | Ek et al. |
| 8,968,326 B2 | 3/2015 | Mani et al. |
| 8,974,458 B2 | 3/2015 | Long et al. |
| 8,974,468 B2 | 3/2015 | Borja |
| 8,974,537 B2 | 3/2015 | Dreyfuss |
| 9,005,287 B2 | 4/2015 | Stone |
| 9,011,452 B2 | 4/2015 | Iannotti et al. |
| 9,011,537 B2 | 4/2015 | Wei et al. |
| 9,044,345 B2 | 6/2015 | Warkentine et al. |
| 9,078,770 B2 | 7/2015 | Smith et al. |
| 9,084,685 B2 | 7/2015 | Huff et al. |
| 9,089,432 B1 | 7/2015 | Henderson |
| 9,089,435 B2 | 7/2015 | Walch et al. |
| 9,089,440 B2 | 7/2015 | Mueller |
| 9,095,439 B2 | 8/2015 | Lian |
| 9,132,012 B2 | 9/2015 | Klotz et al. |
| 9,161,839 B2 | 10/2015 | Flom et al. |
| 9,173,740 B2 | 11/2015 | Gradel |
| 9,192,477 B2 | 11/2015 | Slater et al. |
| 9,198,776 B2 | 12/2015 | Young |
| 9,211,127 B2 | 12/2015 | Stamp |
| 9,220,572 B2 | 12/2015 | Meridew et al. |
| 9,241,720 B2 | 1/2016 | Forsell |
| 9,247,998 B2 | 2/2016 | Hladio et al. |
| 9,271,847 B2 | 3/2016 | Murphy |
| 9,289,218 B2 | 3/2016 | Courtney, Jr. et al. |
| 9,298,313 B2 | 3/2016 | Preuss |
| 9,301,857 B2 | 4/2016 | Matyas et al. |
| D757,269 S | 5/2016 | Prybyla et al. |
| 9,326,781 B2 | 5/2016 | Iannotti et al. |
| 9,339,277 B2 | 5/2016 | Jansen et al. |
| 9,339,393 B2 | 5/2016 | Collins |
| 9,351,841 B2 | 5/2016 | Meier et al. |
| 9,402,727 B2 | 8/2016 | Stubbs |
| 9,402,730 B2 | 8/2016 | Lederman et al. |
| 9,402,731 B2 | 8/2016 | Winslow et al. |
| 9,402,742 B2 | 8/2016 | Cannell |
| 9,402,746 B2 | 8/2016 | Boyer et al. |
| 9,433,508 B2 | 9/2016 | Phipps |
| 9,445,911 B2 | 9/2016 | Long et al. |
| 9,468,538 B2 | 10/2016 | Nycz et al. |
| 9,495,483 B2 | 11/2016 | Steines et al. |
| 9,498,344 B2 | 11/2016 | Hodorek et al. |
| 9,504,578 B2 | 11/2016 | Hood et al. |
| 9,522,067 B2 | 12/2016 | Frankle |
| 9,526,512 B2 | 12/2016 | Sharp et al. |
| 9,526,632 B2 | 12/2016 | Walsh et al. |
| 9,532,730 B2 | 1/2017 | Wasielewski |
| 9,532,880 B2 | 1/2017 | Lappin |
| 9,566,162 B2 | 2/2017 | Isch |
| 9,572,682 B2 | 2/2017 | Aghazadeh |
| 9,687,586 B2 | 6/2017 | Morrey et al. |
| 9,763,790 B2 | 9/2017 | Grappiolo et al. |
| 9,770,336 B2 | 9/2017 | Forsell |
| 9,855,153 B2 | 1/2018 | Unwin et al. |
| 10,064,725 B2 | 9/2018 | Carr et al. |
| 10,092,419 B2 | 10/2018 | Hananouchi et al. |
| 10,765,529 B2* | 9/2020 | Kukkar ............... A61F 2/4465 |
| 11,103,355 B2 | 8/2021 | Forsell |
| 11,173,047 B2* | 11/2021 | Milz .................... A61F 2/4465 |
| 2001/0047210 A1 | 11/2001 | Wolf |
| 2002/0038123 A1 | 3/2002 | Visotsky et al. |
| 2003/0044226 A1 | 3/2003 | Cloyd |
| 2003/0055507 A1 | 3/2003 | Mcdevitt et al. |
| 2003/0125810 A1 | 7/2003 | Sullivan et al. |
| 2003/0130741 A1 | 7/2003 | Mcminn |
| 2004/0010261 A1 | 1/2004 | Hoag et al. |
| 2004/0015238 A1 | 1/2004 | Buehler et al. |
| 2004/0172039 A1 | 9/2004 | Dye |
| 2005/0065617 A1 | 3/2005 | Moctezuma De La Barrera et al. |
| 2005/0187562 A1 | 8/2005 | Grimm et al. |
| 2006/0184249 A1 | 8/2006 | Tarabishy |
| 2006/0189864 A1 | 8/2006 | Paradis et al. |
| 2006/0235539 A1 | 10/2006 | Blunn et al. |
| 2007/0043367 A1 | 2/2007 | Lawrie |
| 2007/0098549 A1 | 5/2007 | Nies |
| 2007/0179625 A1 | 8/2007 | Ekholm et al. |
| 2007/0179630 A1 | 8/2007 | Benedict et al. |
| 2007/0244565 A1 | 10/2007 | Stchur |
| 2008/0009951 A1 | 1/2008 | Hodge |
| 2008/0015708 A1 | 1/2008 | Howie et al. |
| 2008/0033571 A1 | 2/2008 | Tuke |
| 2008/0077150 A1* | 3/2008 | Nguyen ............ A61B 17/1671 606/85 |
| 2008/0119944 A1 | 5/2008 | Bruce et al. |
| 2008/0269596 A1 | 10/2008 | Revie et al. |
| 2009/0099566 A1 | 4/2009 | Maness et al. |
| 2009/0222007 A1 | 9/2009 | Bos et al. |
| 2010/0114326 A1 | 5/2010 | Winslow et al. |
| 2010/0137870 A1 | 6/2010 | Shea et al. |
| 2010/0191246 A1 | 7/2010 | Howald et al. |
| 2010/0217270 A1 | 8/2010 | Polinski et al. |
| 2010/0298834 A1 | 11/2010 | Hildebrandt |
| 2011/0009976 A1 | 1/2011 | Cruchet |
| 2011/0077650 A1 | 3/2011 | Braun et al. |
| 2011/0224673 A1 | 9/2011 | Smith |
| 2012/0041563 A1 | 2/2012 | Chudik |
| 2012/0130387 A1* | 5/2012 | Simpson ............. A61F 2/4611 606/104 |

(56) References Cited

U.S. PATENT DOCUMENTS

| | | |
|---|---|---|
| 2012/0290099 A1 | 11/2012 | Gibson et al. |
| 2013/0030543 A1 | 1/2013 | Morrey et al. |
| 2013/0261681 A1 | 10/2013 | Bittenson |
| 2014/0018815 A1 | 1/2014 | Kirschman |
| 2014/0114179 A1 | 4/2014 | Mller et al. |
| 2014/0135781 A1 | 5/2014 | Chana et al. |
| 2014/0277540 A1 | 9/2014 | Leszko et al. |
| 2015/0057666 A1 | 2/2015 | Kelley |
| 2015/0094780 A1 | 4/2015 | Krickeberg et al. |
| 2015/0257888 A1 | 9/2015 | Acker et al. |
| 2015/0328015 A1 | 11/2015 | Olson et al. |
| 2015/0342754 A1 | 12/2015 | Geebelen et al. |
| 2015/0359544 A1 | 12/2015 | Pressacco et al. |
| 2015/0366601 A1 | 12/2015 | Hoeppner |
| 2016/0022286 A1 | 1/2016 | Borries et al. |
| 2016/0038243 A1 | 2/2016 | Miller et al. |
| 2016/0038244 A1 | 2/2016 | Netravali et al. |
| 2016/0038307 A1 | 2/2016 | Bettenga |
| 2016/0106552 A1 | 4/2016 | Cardamone et al. |
| 2016/0166390 A1 | 6/2016 | Dye et al. |
| 2016/0175109 A1 | 6/2016 | Reu et al. |
| 2016/0199199 A1 | 7/2016 | Pedicini |
| 2016/0228264 A1 | 8/2016 | Anthony et al. |
| 2016/0250039 A1 | 9/2016 | Chow |
| 2016/0270836 A1 | 9/2016 | Ferreira et al. |
| 2016/0287396 A1 | 10/2016 | Huff et al. |
| 2016/0324648 A1 | 11/2016 | Hodorek et al. |
| 2016/0331551 A1 | 11/2016 | Slade et al. |
| 2016/0338751 A1 | 11/2016 | Kellar et al. |
| 2016/0374813 A1 | 12/2016 | Tepic |
| 2017/0020686 A1 | 1/2017 | Baird |
| 2017/0042700 A1 | 2/2017 | Wagner |
| 2017/0049573 A1 | 2/2017 | Hodorek et al. |
| 2017/0367714 A1 | 12/2017 | McCulloch |

FOREIGN PATENT DOCUMENTS

| | | |
|---|---|---|
| AU | 2002310193 A1 | 12/2002 |
| AU | 2002237866 A8 | 4/2003 |
| AU | 2007202573 A1 | 6/2007 |
| AU | 2005200196 B2 | 3/2008 |
| AU | 2011239283 B2 | 8/2013 |
| AU | 2011244995 B2 | 1/2015 |
| AU | 2015203808 A1 | 7/2015 |
| AU | 2016201044 A1 | 3/2016 |
| AU | 2016206236 A1 | 8/2016 |
| AU | 2014200032 B9 | 9/2016 |
| AU | 2016250396 A1 | 11/2016 |
| BE | 1020070 A5 | 4/2013 |
| CA | 1239501 A1 | 7/1988 |
| CA | 2013746 C | 10/1999 |
| CA | 2569572 A1 | 5/2008 |
| CH | 555673 A | 11/1974 |
| CH | 704310 A2 | 7/2012 |
| CN | 1207029 A | 2/1999 |
| CN | 201299670 Y | 9/2009 |
| CN | 201701337 U | 1/2011 |
| CN | 102018554 A | 4/2011 |
| CN | 102579168 A | 7/2012 |
| CN | 202724048 U | 2/2013 |
| CN | 202724049 U | 2/2013 |
| CN | 103735303 A | 4/2014 |
| CN | 203873867 U | 10/2014 |
| DE | 2621666 A1 | 11/1977 |
| DE | 2726297 A1 | 12/1978 |
| DE | 2842847 C2 | 12/1983 |
| DE | 3613657 A1 | 11/1987 |
| DE | 3741489 A1 | 6/1989 |
| DE | 3829361 C2 | 3/1990 |
| DE | 3923154 C2 | 7/1991 |
| DE | 4116507 C1 | 9/1992 |
| DE | 9212846 U1 | 1/1993 |
| DE | 4439309 A1 | 3/1996 |
| DE | 4441870 C1 | 3/1996 |
| DE | 29701082 U1 | 7/1998 |
| DE | 69416701 | 4/1999 |
| DE | 19811820 A1 | 11/1999 |
| DE | 29907259 U1 | 11/1999 |
| DE | 29907341 U1 | 11/1999 |
| DE | 19804065 A1 | 12/1999 |
| DE | 19826306 C2 | 2/2000 |
| DE | 10223474 A1 | 12/2003 |
| DE | 10233204 A1 | 1/2004 |
| DE | 202005001040 U1 | 5/2005 |
| DE | 19548154 A1 | 7/2005 |
| DE | 19548154 B4 | 7/2005 |
| DE | 202007014948 U1 | 1/2008 |
| DE | 102009024654 A1 | 12/2010 |
| DE | 102009043311 A1 | 3/2011 |
| DE | 102011101054 A1 | 2/2012 |
| DE | 202012104671 U1 | 5/2013 |
| DE | 202012104673 U1 | 5/2013 |
| EP | 25814 B1 | 5/1984 |
| EP | 112435 B1 | 1/1987 |
| EP | 145938 B1 | 5/1988 |
| EP | 290375 A1 | 11/1988 |
| EP | 181360 B1 | 8/1989 |
| EP | 408109 A1 | 1/1991 |
| EP | 399920 B1 | 10/1992 |
| EP | 655229 A1 | 5/1995 |
| EP | 645127 B1 | 1/1996 |
| EP | 700670 A1 | 3/1996 |
| EP | 550117 B1 | 5/1996 |
| EP | 550118 B1 | 7/1996 |
| EP | 528284 B1 | 10/1996 |
| EP | 611225 B1 | 9/1997 |
| EP | 797964 A1 | 10/1997 |
| EP | 968693 A2 | 1/2000 |
| EP | 1025817 A1 | 8/2000 |
| EP | 1360949 A1 | 11/2003 |
| EP | 1464304 A2 | 10/2004 |
| EP | 1566155 A1 | 8/2005 |
| EP | 1776937 B1 | 6/2009 |
| EP | 1885294 B1 | 3/2014 |
| EP | 2410952 B1 | 8/2014 |
| ES | 2023134 B3 | 1/1992 |
| FR | 2578738 A1 | 9/1986 |
| FR | 2581336 A1 | 11/1986 |
| FR | 2598609 A1 | 11/1987 |
| FR | 2602672 A1 | 2/1988 |
| FR | 2715830 A1 | 8/1995 |
| FR | 2925857 B1 | 3/2010 |
| FR | 2925841 B1 | 8/2011 |
| FR | 2932678 B1 | 12/2011 |
| FR | 2924771 B1 | 12/2012 |
| FR | 2970170 B1 | 12/2012 |
| FR | 2963733 B1 | 6/2013 |
| FR | 2986150 B1 | 2/2014 |
| FR | 2996119 B1 | 9/2015 |
| FR | 3020941 A1 | 11/2015 |
| GB | 1245669 A | 9/1971 |
| GB | 1371335 A | 10/1974 |
| GB | 2033755 A | 5/1980 |
| GB | 2118043 B | 1/1985 |
| GB | 2197204 B | 8/1990 |
| GB | 2216015 B | 10/1991 |
| GB | 2277448 A | 11/1994 |
| GB | 2315679 B | 6/1998 |
| GB | 2341554 B | 8/2000 |
| GB | 2372707 A | 9/2002 |
| GB | 2407774 A | 5/2005 |
| GB | 2406055 B | 7/2007 |
| GB | 2459285 A | 10/2009 |
| GR | 1006033 B | 9/2008 |
| IN | 200400886 P2 | 5/2006 |
| IN | 200702523 P1 | 7/2007 |
| IN | 200201035 P4 | 8/2007 |
| IN | 200701428 I4 | 11/2008 |
| IN | 200801724 I2 | 6/2009 |
| IN | 201102418 P2 | 11/2012 |
| IN | 201201444 P4 | 3/2013 |
| IN | 201204069 P2 | 6/2013 |
| IN | 201301126 P2 | 9/2013 |
| IN | 201300437 P4 | 6/2014 |

(56) References Cited

FOREIGN PATENT DOCUMENTS

| | | |
|---|---|---|
| IN | 201308495 P1 | 12/2014 |
| IN | 201302828 I1 | 2/2015 |
| IN | 201300244 P4 | 5/2016 |
| IN | 201310687 P1 | 5/2016 |
| JP | 53017347 A | 2/1978 |
| JP | H 4-501223 A | 3/1992 |
| JP | 06305629 A | 11/1994 |
| JP | 11047137 A | 2/1999 |
| JP | 3185273 U | 7/2001 |
| JP | 2001238901 A | 9/2001 |
| JP | 04361339 B2 | 11/2009 |
| JP | 51023333 B2 | 1/2013 |
| JP | 2014104195 A | 6/2014 |
| JP | 2017038949 A | 2/2017 |
| KR | 199603527 B1 | 3/1996 |
| KR | 2001082116 A | 8/2001 |
| KR | 2001087178 A | 9/2001 |
| KR | 2002070994 A | 9/2002 |
| RU | 2574375 C2 | 2/2016 |
| WO | 8802246 A2 | 4/1988 |
| WO | 9003769 A1 | 4/1990 |
| WO | 9503758 A1 | 2/1995 |
| WO | 95003758 A1 | 2/1995 |
| WO | 9617553 A1 | 6/1996 |
| WO | 9810720 A1 | 3/1998 |
| WO | 0003664 A1 | 1/2000 |
| WO | 0009038 A2 | 2/2000 |
| WO | 0009044 A1 | 2/2000 |
| WO | 0015155 A1 | 3/2000 |
| WO | 0023009 A1 | 4/2000 |
| WO | 0110356 A2 | 2/2001 |
| WO | 0217822 A1 | 3/2002 |
| WO | 03034955 A1 | 5/2003 |
| WO | 03075801 A1 | 9/2003 |
| WO | 2005025451 A2 | 3/2005 |
| WO | 2005079710 A1 | 9/2005 |
| WO | 2006/020803 A2 | 2/2006 |
| WO | 2006024840 A1 | 3/2006 |
| WO | 2006076962 A2 | 7/2006 |
| WO | 2006084426 A2 | 8/2006 |
| WO | 2006092613 A2 | 9/2006 |
| WO | 2007093695 A1 | 8/2007 |
| WO | 2007/098549 A1 | 9/2007 |
| WO | 2009037284 A2 | 3/2009 |
| WO | 2009056804 A2 | 5/2009 |
| WO | 2011150180 A2 | 12/2011 |
| WO | 2012006508 A2 | 1/2012 |
| WO | 2012021849 A2 | 2/2012 |
| WO | 2015187876 A1 | 12/2015 |

OTHER PUBLICATIONS

Japanese Notification of Refusal for Corresponding Japanese Patent Application 2021-518494, Dated Apr. 27, 2023, 13 Pages.
Search and Examination Report From Corresponding GB Patent Application GB1816197.6, Dated Mar. 28, 2019, 6 Pages.
European International Search Report for PCT/EP2019/076812—dated Jan. 1, 2020.

* cited by examiner

PROSTHESIS EXTRACTION SYSTEM

CROSS-REFERENCE TO RELATED APPLICATIONS

This application is a National Stage Application filed Under 35 U.S.C. § 371 of International Application No. PCT/EP2019/076812 filed Oct. 3, 2019, which claims priority to GB 1816197.6 filed Oct. 4, 2018, both of which are hereby incorporated by reference in their entireties.

TECHNICAL FIELD

The present disclosure relates to a device for extraction of a prosthetic component from a patient during surgery. Particular configurations relate to a femoral stem prosthesis extractor component for removing the femoral stem of a prosthetic hip joint from a femur of a patient during surgery. A system of apparatus components for extraction of a prosthetic from a patient during surgery is also described. In addition, this disclosure also describes a method of extracting and a method of implanting a prosthetic component, such as a femoral stem prosthesis, from a patient during surgery.

BACKGROUND

Prosthetic implants, such as prosthetic hip joints, are well known in the art. Typically, at least one component of a prosthetic implant is anchored in a bone of a patient. For example, in the case of a prosthetic hip joint, a femoral stem component is inserted and anchored in the femur of a patient. A neck portion extends from the femoral stem on which a femoral head is mounted. The femoral head is configured to couple with an acetabular cup component to form the prosthetic hip joint.

During surgery, the femur of a patient is prepared to receive the femoral stem component of the prosthetic hip. The femoral stem must be positioned correctly to align with the acetabular cup component. Angular orientation and length are both important. As such, a surgeon may be required to insert the femoral stem component into the femur of a patient after initial preparations of the femoral canal, and then extract the femoral stem to perform additional femoral canal preparation prior to re-inserting the femoral stem. This procedure may need to be repeated until a satisfactory positioning of the femoral stem is achieved.

During such intra-operative femoral stem removal, it is generally necessary to use an instrument to retrieve the stem due to positive fixation of the stem within the femur. The extraction instrument is required to be coupled to the femoral stem to pull the stem from the femur. However, using such an instrument to remove the stem can cause damage to the stem, which is undesirable, especially if the stem is to be re-inserted following additional femoral canal preparation. The procedure for femoral stem removal is particularly challenging in anterior surgery where access to the stem is limited. Issues such as cross threading, general damage, or failure of the instruments can result. Such problems can also apply when removing a femoral stem during revision surgery in addition to intra-operative primary surgery. Similar problems can also apply when extracting other types of prosthetic component. Furthermore, in addition to damage caused to the prosthetic component during such an extraction procedure, undue damage to bone and surrounding tissue should also be avoided.

It is an aim of the present disclosure to address the aforementioned problems.

SUMMARY

According to one aspect of the disclosure as described herein there is provided a surgical device for extraction of a prosthetic component from a patient during surgery, the surgical device comprising:
- a first component having a female coupling portion at a first end, and a second end configured to be connected to one of a prosthetic component or a surgical extraction instrument, the first component further including a retainer; and
- a second component having a first end defining a male coupling portion, a stem extending from the male coupling portion, and a second end configured to be connected to the other of the prosthetic component or the surgical extraction instrument,
- wherein the male coupling portion of the second component is configured to be disposed within the female coupling portion of the first component and retained within the female coupling portion by the retainer with the stem of the second component extending away from the female coupling portion of the first component, the male coupling portion of the second component and the retainer of the first component being configured such that the male coupling portion is held in the female coupling portion while allowing articulation of the first component relative to the second component,
- the first and second components forming an articulating joint allowing a user to connect the surgical extraction instrument to the prosthetic component in a patient, articulate a portion of the surgical extraction instrument which resides external from the operating site, and transfer extraction forces to enable removal of the prosthetic component from the patient.

In some examples, at least one of the first component and the second component further comprises a driver component for driving attachment of the said component to the prosthetic component.

In certain examples, the device includes a ball and socket joint. For example, a surgical device for extraction of a prosthetic component from a patient during surgery can be provided, wherein the female coupling portion of the surgical device can be a socket and the male coupling portion can be a ball portion which is configured to be disposed within the socket, the socket having a closed end and an open end, and the retainer of the first component being a neck portion disposed between the closed end and the open end of the socket and defining a narrow internal width compared to a width of the closed end of the socket, wherein the ball portion is configured to be disposed within the socket with the stem of the second component extending through the neck portion and out through the open end of the socket, the ball portion having a width which is larger than the width of the neck portion such that the ball portion is held in the closed end of the socket and prevented from passing out through the neck portion and open end of the socket while allowing relative articulation of the ball portion and socket, the ball portion and socket thus forming a ball and socket joint. The ball and socket joint allows a user to connect the surgical extraction instrument to the prosthetic component in a patient, articulate a portion of the surgical extraction instrument which resides external from the operating site, and transfer extraction forces to enable removal of the prosthetic component from the patient.

The aforementioned configuration enables the surgical extraction instrument (e.g. a slide hammer) to be articulated relative to the prosthetic component while also transferring extraction forces to enable removal of the prosthetic component from the patient. The articulation functionality enables use in all approaches and incision sizes. Furthermore, by allowing articulation and extraction force transfer, issues such as cross threading, general damage, or failure of the instruments are alleviated. Furthermore, in addition to alleviation of damage caused to the prosthetic component during such an extraction procedure, undue damage to bone and surrounding tissue is also alleviated.

One of the socket and the ball portion may be permanently attached to the extraction instrument or alternatively may be removably attachable to the extraction instrument.

Embodiments described in the detailed description are removably attached to an extraction instrument. However, it is also envisaged that the ball and socket device could be permanently integrated at the end of an extraction instrument.

The socket can be configured to be attached to the surgical extraction instrument and the ball portion can be configured to be attached to the prosthetic component. Embodiments having this configuration are described in the detailed description. However, it is also envisaged that in principle the order of the components can be reversed so that the ball portion is configured to be attached to the surgical extraction instrument and the socket is configured to be attached to the prosthetic component.

The socket can comprise an opening in the side wall thereof, the opening having a complementary shape to that of the ball portion to enable the ball portion to be coupled and uncoupled from the socket. Advantageously, the opening in the side wall of the socket is located such that when applying extraction forces to enable removal of the prosthetic component from the patient in use, the ball portion cannot slide sideways out of the opening in the side wall. That is, after coupling of the ball portion into the socket by moving the ball portion laterally through the opening in the side wall of the socket, the socket can slide axially over the ball portion to a position in which the ball portion cannot move laterally out of the opening in the side wall of the socket.

The driver component can include a drive connector disposed on the second component between the stem and the second end, the drive connector defining a surface for gripping and rotating the second component to attach and release the second component from the prosthetic component.

The first component can also include a drive connector disposed on an internal surface of the side wall between the neck portion and the open end of the first component, the drive connector of the first component having a surface which is complementary to the drive connector on the second component. The socket can be configured to slide over the second component to engage the drive connectors to enable the second component to be driven to connect the second component to the prosthetic component in an attachment configuration, the first component being configured to slide back over the second component in an opposite direction to disengage the drive connectors in an extraction configuration when transferring extraction forces to enable removal of the prosthetic component from the patient. The drive connectors on the first component and the second component can comprise complementary splines. By separating the drive connectors in the extraction configuration this prevents damage to the drive components (e.g. splines) while transmitting extraction forces during the prosthetic extraction procedure.

As an alternative to the use of spline components for driving connection of the ball and socket joint to the prosthetic, the drive connector on the second component may alternatively be a hex connector. Furthermore, the drive connector on the second component may be driven by a complementary connector in the first component or alternatively may be driven be a separate tool such as a hex drive tool. Further still, additionally or alternatively to the drive connector between the stem and the end of the second component, the ball portion may further comprise a drive component for driving attachment of the second component to the prosthetic component. For example, the ball portion may comprise a hex drive. In certain examples, both the drive connector on the ball portion and the drive connector on the stem of the second component are provided such that if one of the drive connectors fails, such as due to undue rounding during use, the other one of the drive connectors can be used to attach or remove the second component from the prosthetic.

The end connector on the second end of the second component may comprise a threaded connector for attachment of the second component to a complementary threaded connector in the prosthetic component. To limit the possibility of cross threading during attachment, the second end of the second component may include an unthreaded lead portion to provide good alignment of components prior to thread engagement.

Other configurations are also envisaged for coupling and driving attachment of the articulating joint components to a prosthetic. For example, the ball portion may comprise a cavity and the socket may comprise a complementary projection, wherein the socket is configured to slide over the second component to engage the projection with the cavity to enable the components to be driven to connect the articulating joint components to the prosthetic component in an attachment configuration, the first component being configured to slide back over the second component in an opposite direction to disengage the projection and cavity in an extraction configuration when transferring extraction forces to enable removal of the prosthetic component from the patient. In one configuration, the projection is in the form of a rod and the cavity is in the form of a groove in the ball portion.

Alternatively still, the female coupling portion of the first component can be in the form of a socket defined by two arms extending from the second end of the first component and having an open end, and the male coupling portion of the second component can be in the form of a ring. In this configuration, the ring is disposable within the socket such that the stem of the second component extends from the ring and out through the open end of the socket. The retainer of the first component can be in the form of a rod which is configured to extend through the ring of the second component to couple the first and second components together while allowing articulation of the first component relative to the second component.

Yet another possibility is a universal joint arrangement. In such an arrangement, the male coupling portion of the second component is in the form of a rotatable member mounted on a first rod, such that the rotatable member is rotatable around a first axis, the rotatable member being disposed within the female coupling portion of the first component, and the retainer of the first component is in the form of a second rod oriented such that the rotatable member is rotatable around a second axis perpendicular to the first axis, the first and second components thus forming a universal joint.

According to another aspect of the present disclosure as described herein, there is provided a surgical system comprising:
- the surgical device as previously defined; and
- a surgical extraction instrument (e.g. a slide hammer) configured to couple to one of the first (e.g. socket) component or the second (e.g. ball) component.

The system may further comprise a prosthetic component configured to couple to the other of the first (e.g. socket) component and the second (e.g. ball) component. For example, this may be in the form of a femoral stem with a suitable connector at an end thereof for coupling to the articulating joint components and surgical extraction instrument.

Also described herein is a method of extracting a prosthetic component from a patient during surgery using the surgical system as defined above, the method comprising:
- coupling together the surgical device, the surgical extraction instrument, and the prosthetic component; and
- extracting the prosthetic component by applying an extraction force to the surgical extraction instrument.

In another example of the above method, the first and second components can be pre-assembled prior to attachment to the extraction instrument.

In a further example, one of the first and second components can be attached the prosthetic within a patient, and the other of the first or second components can then be coupled to the other of the first or second component attached to the prosthetic prior to extraction of the prosthetic component.

According to another aspect of the present disclosure as described herein, there is provided a surgical system comprising:
- the surgical device as previously defined; and
- a surgical implantation instrument configured to couple to one of the first (e.g. socket) component or the second (e.g. ball) component. For example, this may be in the form of a femoral stem with a suitable connector at an end thereof for coupling to the articulating joint components and surgical implantation instrument.

Also described herein is a method of implanting a prosthetic component into a patient during surgery using the surgical system as defined above, the method comprising:
- coupling together the surgical device, the surgical implantation instrument, and the prosthetic component; and
- implanting the prosthetic component by applying an implantation force to the surgical implantation instrument.

In another example of the above method, the first and second components can be pre-assembled prior to attachment to the implantation instrument.

In another example, the prosthetic component can be provided with one of the first and second joint components already attached.

BRIEF DESCRIPTION OF THE DRAWINGS

Embodiments of the present disclosure are described by way of example only with reference to the accompanying drawings in which.

DETAILED DESCRIPTION

Devices as described herein can be used to remove a femoral stem during primary surgery and can also be used for revision surgery. The configurations as described herein allow the same device to work for all approaches and incision sizes by allowing the user to articulate a portion of an extractor which resides external from the operating site, this also being the area which allows for the transfer of extraction forces to enable removal.

Figure 1:
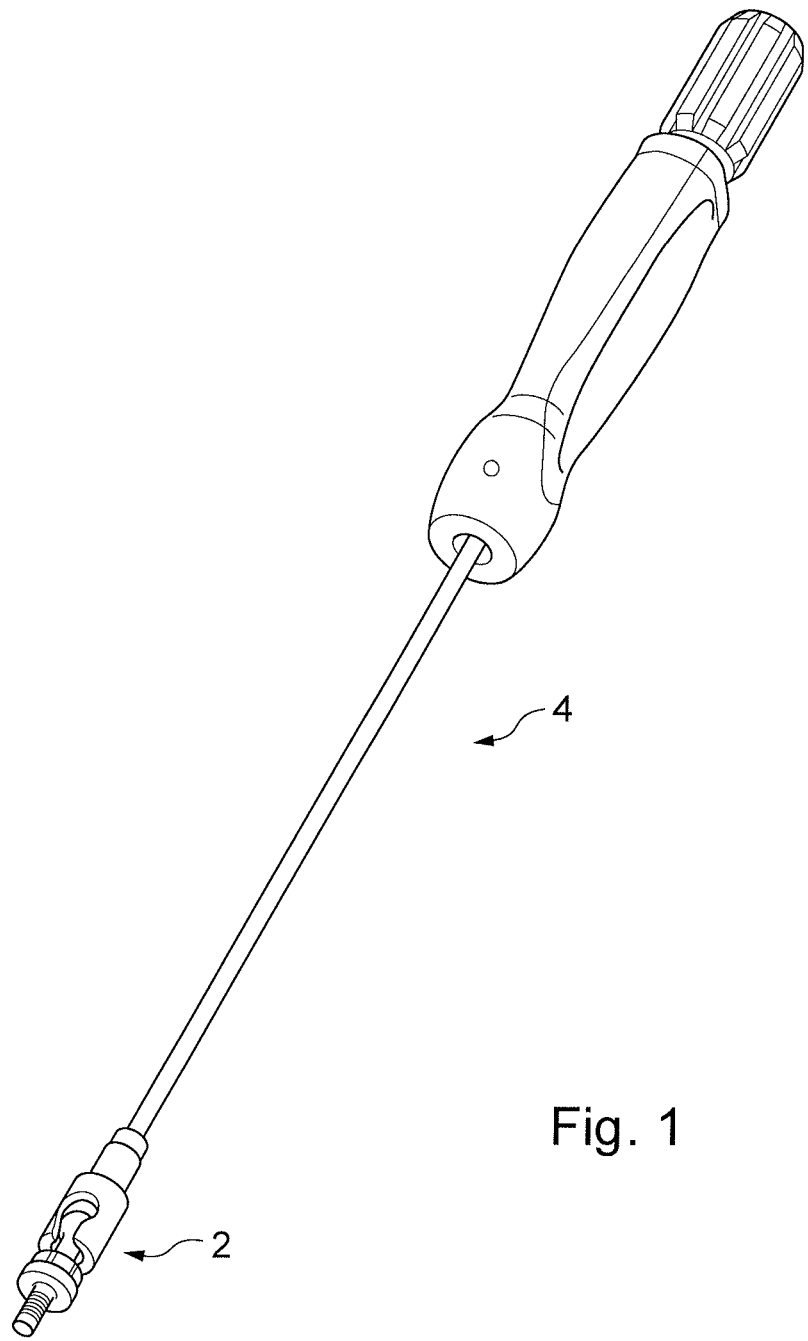
FIG. 1 shows a device for extraction of a prosthetic component from a patient, the device being connected to a slide hammer and connectable to a prosthetic component (not shown) for prosthesis extraction.

FIG. 1 shows a device 2 for extraction of a prosthetic component from a patient, the device 2 being connected to a slide hammer 4 and connectable to a prosthetic component (not shown) for prosthesis extraction. The device is primarily a ball and socket joint to allow pivoting of what is generally a long shaft away from impingement on tissue. The second component attaches to a femoral implant by means, for example, of a thread although in principle it can be attached in numerous ways depending on the approach and variant. The first component has a socket which is separable from the ball by means of a cutout or opening. The first component is either permanently combined or removably connected to the force transmitting part of the device system. The force transmitting device can be a slide or slap hammer as illustrated in FIG. 1 to control the extraction forces more so than hammer blows, but a hammer strike plate could also be used. The first component can be attached to the second component by aligning the socket opening concentric to the ball portion, the socket can then be rotated into the same axis as the screw which captures the ball ready for attachment or extraction.

Figure 2:
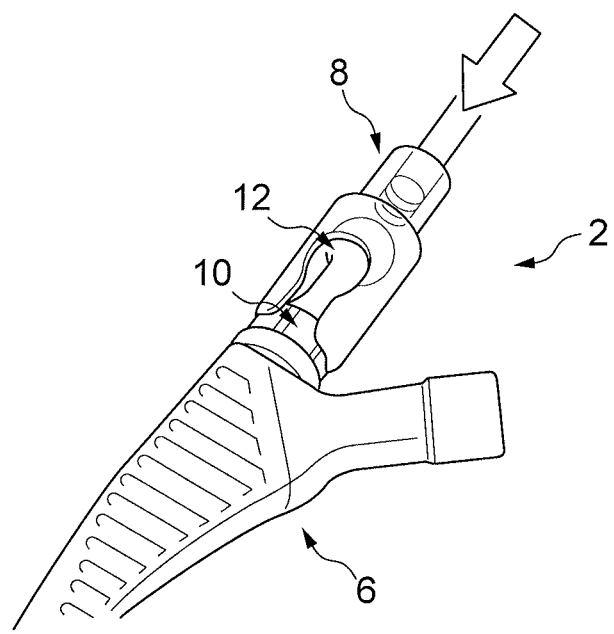
FIG. 2 shows another view of the device of FIG. 1 in the process of being connected to a prosthetic component, an arrow indicating the direction of push to engage the device to drive attachment of the device to the prosthetic component (attachment configuration)

FIG. 2 shows another view of the device 2 in the process of being connected to a prosthetic component 6. An arrow indicates the direction of push to engage the device to drive attachment of the device 2 to the prosthetic component 6. The device 2 includes a first component 8 and a second component 10. The second component 10 includes a ball portion, a stem, a spline portion, and a connector screw or thread for connecting to the prosthetic component 6. When pushed in the direction of the arrow, the first component 8 slides over the second component 10 to engage the splines of the second component 10. In this regard, the first component 8 comprises complementary splines on an interior surface thereof which engage with the splines of the second component 10 when pushed into the configuration illustrated in FIG. 2. The device can then be rotated via the slide hammer or other surgical instrument in order to screw the device onto the femoral stem component 6. That is, once the splines are engaged the whole device will allow the user to tighten/loosen the screw into the stem.

In FIG. 2, the opening 12 in the first component 8 is also labelled. In this "attachment configuration" the ball portion is located towards the upper, closed end of the socket rather than being adjacent the opening so as to prevent the second component 10 from decoupling from the first component 8 during the attachment procedure.

Figure 3:
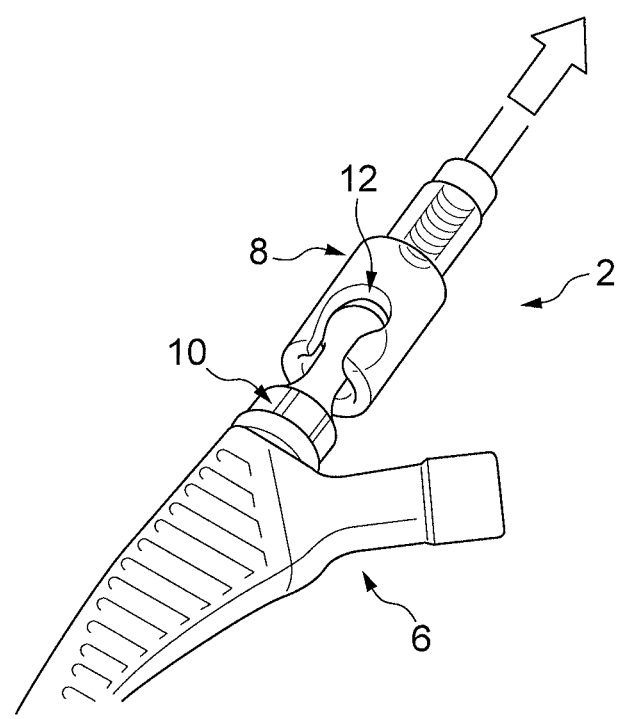
FIG. 3 shows another view of the device of FIGS. 1 and 2 after connection to a prosthetic component, an arrow indicating the direction of pull to extract the prosthetic component (extraction configuration)

FIG. 3 shows another view of the device 2 of FIGS. 1 and 2 after connection to the prosthetic component 6. An arrow indicates the direction of pull to extract the prosthetic component 6. When pulled in this manner, the splines on the interior surface of the first component 8 disengage from the splines on the second component 10. The first component 8 has an interior neck which engages with the ball portion of the second component 10 thereby coupling the first component 8 and second component 10. As such, all of the prosthetic component 6, the second component 10, and the first component 8 are coupled together and all pulled in the direction of the arrow as shown in FIG. 3. That is, once the thread of the second component is locked into the femoral stem 6, the first component 8 can be pulled away axially, disengaging the splines and engaging the underside of the ball portion in an extraction position as illustrated in FIG. 3. Furthermore, with the ball and socket engaged, the device 2 allows for free articulation and rotation of the whole device system (excluding the thread of the second component attached to the femoral stem 6) to miss soft tissue and then start the stem extraction process using, for example, a slap hammer weight.

In FIG. 3, the opening 12 in the first component 8 is also labelled. In this "extraction configuration" the ball portion is located towards the lower, open end of the socket of the first component 8 abutting the internal neck of the first component 8 rather than being adjacent the opening so as to prevent the second component 10 from decoupling from the first component 8 through the opening 12 during the extraction procedure.

Figure 4:
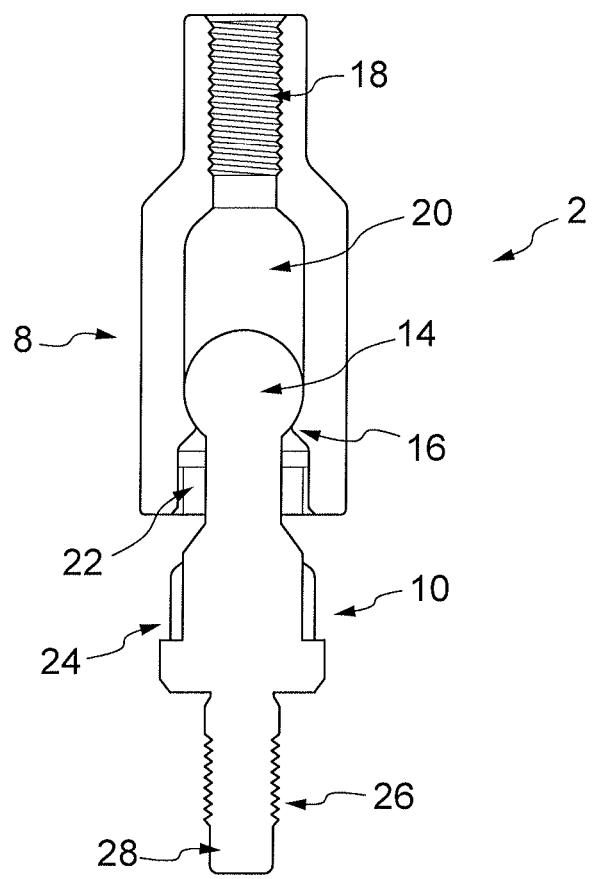
FIG. 4 shows a cross sectional view of the device in its extraction configuration with a ball portion of the second component engaging with a neck portion of the first component to couple the two components together during a pulling action to extract the prosthetic component.

FIG. 4 shows a cross sectional view of the device 2 in its extraction configuration with the ball portion 14 of the second component 10 engaging with a neck portion 16 of the first component 8 to couple the two components together during a pulling action to extract the prosthetic component. The first component comprises an attachment part 18 for attaching the first component 8 to an extraction instrument such as the slide hammer 4 shown in FIG. 1. The first component also has a socket 20 configured to house the ball portion 14 when the first component 8 and second component 10 are coupled together. The neck portion 16 of the first component is between the closed end and the open end 22 of the socket of the first component 8. On an interior wall at the open end 22 of the first component 8, splines are provided as previously described. These splines can be pushed into engagement with splines 24 on the second component as shown in the configuration illustrated in FIG. 2.

Also labelled in FIG. 4 is the threaded connector (e.g. screw or bolt) 26 of the second component which screws into a complementary connector in the prosthetic component which is to be extracted. In the illustrated arrangement, the threaded connector 26 has an extended lead portion 28 which is unthreaded. This aids in preventing cross threading during coupling of the device to the prosthetic component prior to extraction.

Figure 5:
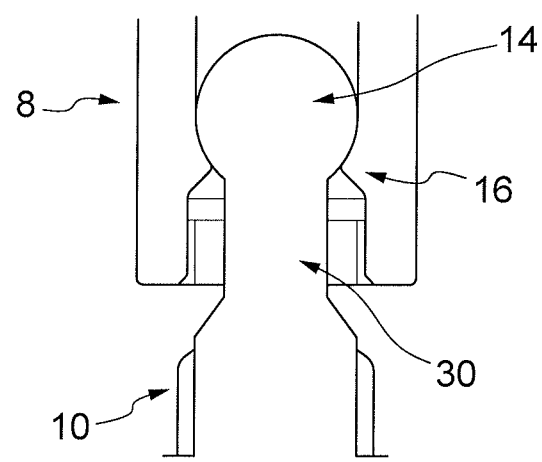
FIG. 5 shows a close-up portion of FIG. 4 illustrating the ball portion of the second component engaging with the neck portion of the socket of the first component to couple the two components together during a pulling action to extract the prosthetic component while also enabling relative articulation of the components.

FIG. 5 shows a close-up portion of FIG. 4 illustrating the ball portion 14 of the second component 10 engaging with the neck portion 16 of the first component 8 to couple the two components together during a pulling action to extract the prosthetic component while also enabling relative articulation of the components. Also labelled is the stem 30 of the second component 10. The stem 30 is somewhat narrower in width when compared to the width of the neck portion 16 in the first component to ensure that the components can be freely articulated without locking together in a fixed angular configuration during the extraction procedure.

Figure 6:
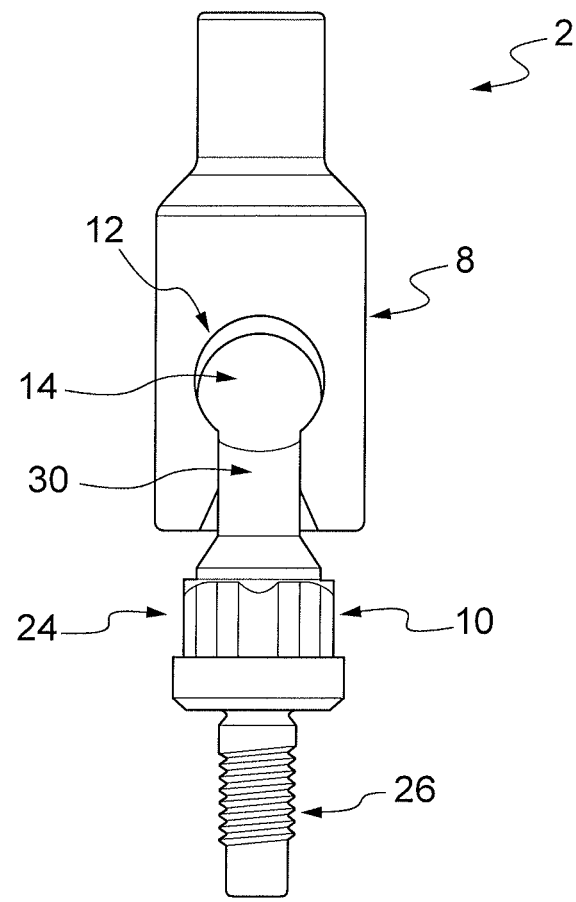
FIG. 6 shows a side view of the device of FIGS. 1 to 5 in isolation of the prosthetic component and extraction instrument, the component being in a neutral configuration between the attachment configuration and the extraction configuration wherein the second component can be disengaged from the first component via a side wall cut-out or opening.

FIG. 6 shows a side view of the device 2 of FIGS. 1 to 5 in isolation of the prosthetic component and extraction instrument. The device 2 is illustrated in a neutral configuration between the attachment configuration and the extraction configuration of preceding Figures. In this neutral position the second component 10 can be moved laterally through an opening 12 in a side wall of the first component 8 in order to engage and disengage the second component 10 and the first component 8. As such, the opening 12 should have a complementary shape to that of the ball portion 14 and stem 30 of the second component 10 so as to allow the ball portion 14 and stem 30 to pass through the opening 12 when moved laterally in this neutral position.

Also labelled in FIG. 6 are the spline portion 24 and screw portion 26 of the second component 10. However, it should be noted that other variants are envisaged. For example, other forms of connectors may be used in place of the splines 24 and screw 26 shown in FIG. 6.

Figure 7:
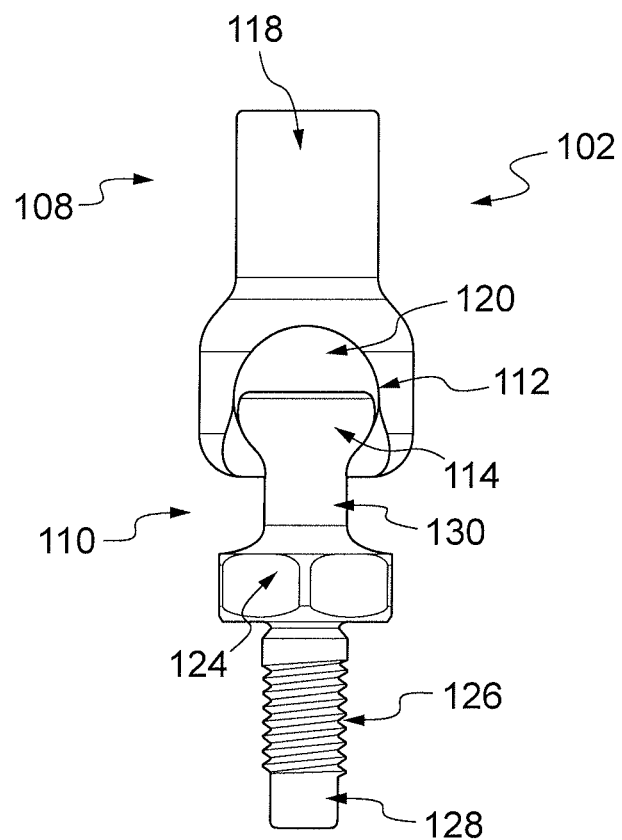
FIG. 7 shows another device for extraction of a prosthetic component from a patient, the device being similar in construction and function to that shown in FIGS. 1 to 6 but with a different coupling structure for driving attachment of the component to a prosthetic.

FIG. 7 shows another device 102 for extraction of a prosthetic component from a patient. The device 102 is similar in construction and function to that of device 2 shown in FIGS. 1 to 6 but with a different coupling structure for driving attachment of the device to a prosthetic component. The device 102 comprises a first component 108 and a second component 110. The first component 108 includes a female coupling portion 118 which is connectable to an extraction instrument such as the slap hammer 4 of FIG. 1. The first component 108 also has a opening 112 which can be used to engage and disengage the first component 108 and the second component 110. The first component 108 defines a socket 120 in which a ball portion is disposed, in this case a hemispherical ball portion 114 of the second component 110.

The second component 110 includes a ball portion 114, a stem 130, a hex 124, and a threaded end connector 126 with an unthreaded lead portion 128. The construction is similar to that of the previous second component but differs in that a hex bolt structure 124 is provided instead of the splines 24 of the previous configuration. Furthermore, a hemispherical ball portion 114 is provided rather than a full ball portion 14 as provided in the previous configuration.

Figure 8:
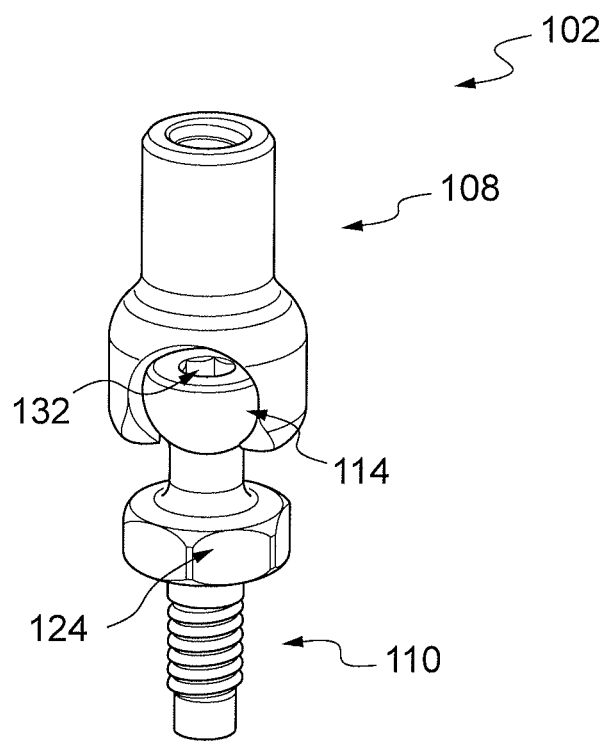
FIG. 8 shows another view of the device of FIG. 7 showing the different coupling structure in the form of a primary hex drive in the ball portion of the second component and a secondary hex drive on the stem of the second component for use if the primary hex drive fails.

FIG. 8 shows another view of the device of FIG. 7 showing a different coupling structure in the form of a hex drive 132 in a flat upper surface of the hemispherical ball portion 114 of the second component 110. The hex drive 132 can be engaged by a suitable screw driver, hex key, or Allen key to attach the second component 110 to the prosthetic component which is to be extracted. In the event that the hex drive 132 fails for any reason, such as undue rounding during use, the hex 124 can be used instead to attach or remove the second component 110 from a prosthetic component. This can be achieved using a separate tool. Alternatively, in certain configurations, the first end of the first component 108 can be configured to have an interior surface which is complementary to the hex 124. In such an alternative arrangement, the first component 108 can be pushed to slide over the second component 110 to engage the hex 124 and rotated for attaching or removing the second component 110 from a prosthetic component in a similar manner to the complementary splines of the previous arrangement described in relation to FIG. 2.

Figure 9:
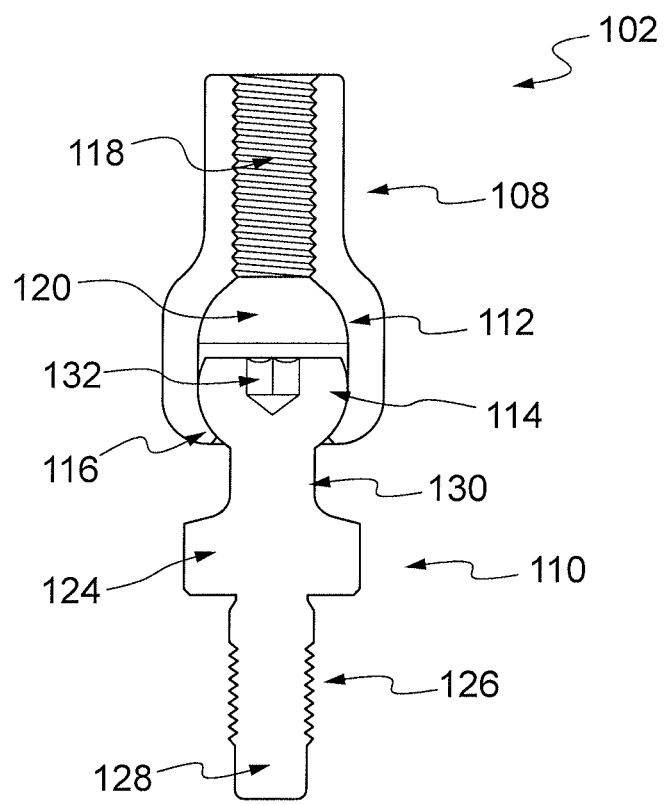
FIG. 9 shows a cross sectional view of the device of FIGS. 7 and 8.

FIG. 9 shows a cross sectional view of the device 102 of FIGS. 7 and 8. As can be seen, the first component 108 comprises a female coupling portion 118 which is connectable to an extraction instrument such as the slap hammer 4 of FIG. 1. The first component 108 also has an opening 112 which can be used to engage and disengage the first component 108 and the second component 110. The first component 108 defines a socket 120 in which a ball portion, or in this case hemispherical portion 114, of the second component 110, is disposed. At a first, open end of the first component, an internal neck portion 116 is provided for engaging the ball portion 114 when extracting the prosthetic via a pulling action. The second component 110 includes a ball portion 114, a stem 130, a hex 124, and a threaded connector 126 with an unthreaded lead portion 128.

Figure 10:
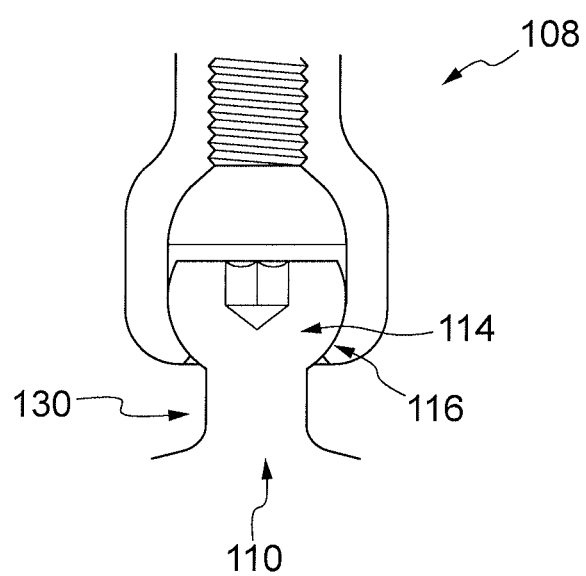
FIG. 10 shows a close-up portion of FIG. 9 illustrating the ball portion of the second component engaging with the neck portion of the socket of the first component to couple the two components together during a pulling action to extract the prosthetic component while also enabling relative articulation of the components.

FIG. 10 shows a close-up portion of FIG. 9 illustrating the ball portion 114 of the second component 110 engaging with the neck portion 116 of the first component 108 to couple the two components together during a pulling action to extract the prosthetic component while also enabling relative articulation of the components. Again, the stem 130 of the second component is somewhat narrower in width when compared to the width of the neck portion 116 in the first component to ensure that the components can be freely articulated without locking together in a fixed angular configuration during the extraction procedure.

The variant illustrated in FIGS. 7 to 10 is much smaller in comparison with the variant illustrated in FIGS. 1 to 6 but uses the same extraction principle. A noticeable difference is the screw attachment which is driven by an auxiliary screw driver with a hex connection. It is envisaged this would be, for example, a flex drive such as shell screw driver which aids with access concerns during insertion of the screw.

Furthermore, while the variant illustrated in FIGS. 7 to 10 has both a hex drive 132 in the second portion and a hex 124 along the stem of the second component, it is also envisaged that only one of these two features may be provided. Either could be used to attached or remove the second component from a prosthetic via a screwing motion. The advantage of providing both is that redundancy is incorporated in the event of failure of one of the mechanisms, e.g. due to undue rounding in use.

While this disclosure has been described above in relation to certain embodiments it will be appreciated that various alternative embodiments can be provided. For example, in both the illustrated embodiments the socket component is attached to an extraction tool and the ball component is attached to the prosthetic which is to be extracted. However, in alternative configurations the components can be reversed such that the second component is attached to the extraction tool and the first component is attached to the prosthetic which is to be extracted. Further still, while both the illustrated embodiments provided threaded connections for attaching the ball and socket device to an extraction tool and prosthetic, in principle other known connections may be utilized. FIGS. 11 to 20 illustrate several alternative configurations which are briefly discussed below.

Figure 11:
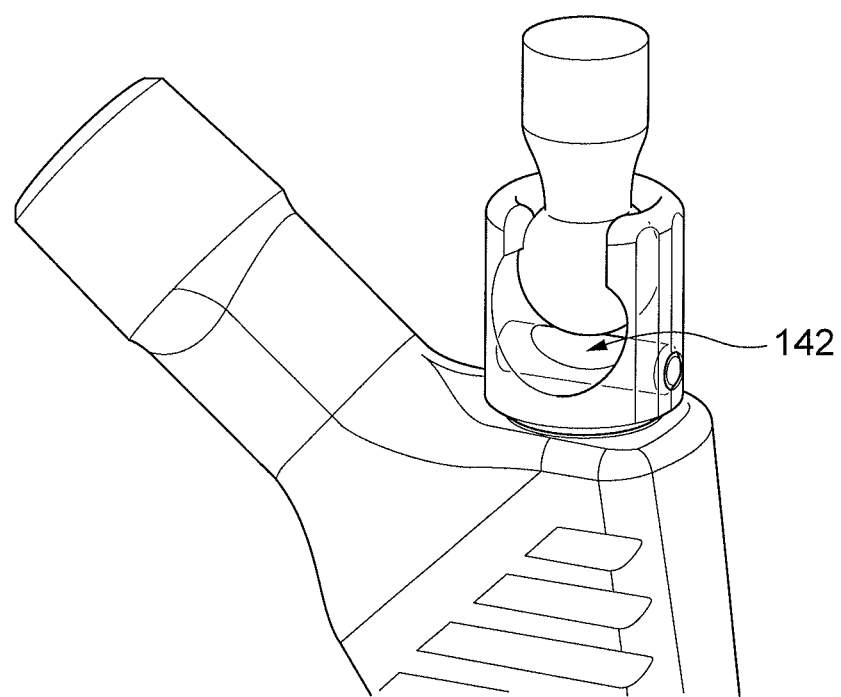
FIG. 11 shows another device for extraction of a prosthetic component from a patient, the device being similar in construction and function to the devices shown in FIGS. 1 to 10 but with a different coupling structure for driving attachment of the component to a prosthetic and with the order of the components reversed such that the first component is attached to the prosthetic and the second component is attachable to an extraction instrument.
Figure 12:
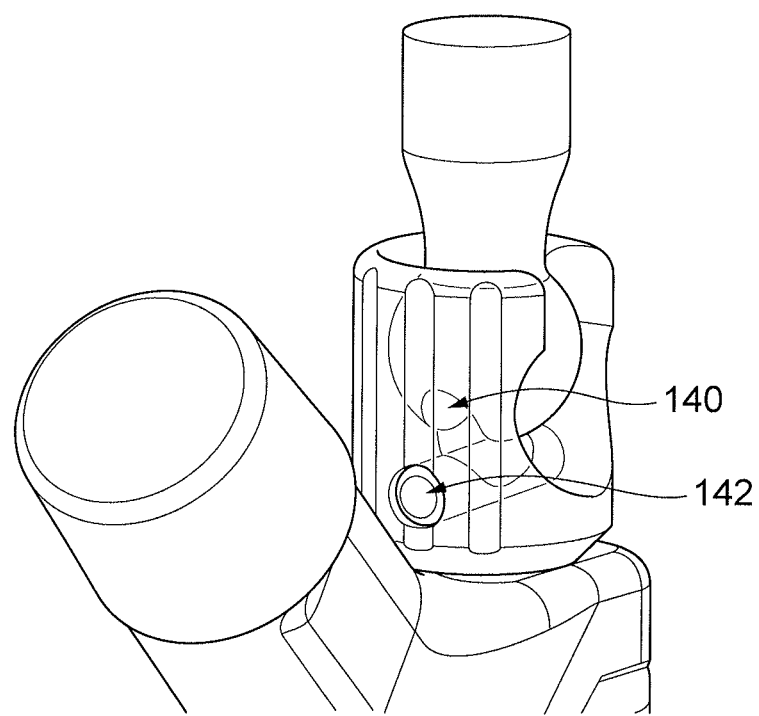
FIG. 12 shows another view of the device of FIG. 11 showing the coupling structure for driving attachment in the form of a groove in the ball portion of the second component and a complementary rod within the socket of the first component.
Figure 13:
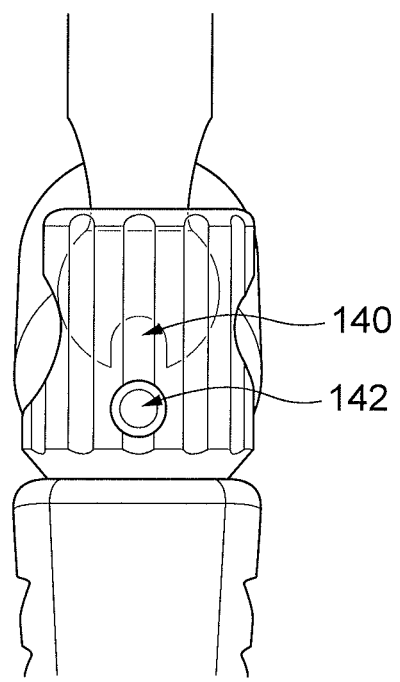
FIG. 13 shows another view of the device of FIGS. 11 and 12.

FIGS. 11 to 13 show several views of another device for extraction of a prosthetic component from a patient. Compared to the previously discussed configurations, the order of the ball and socket components is reversed such that the first component is attached to the prosthetic and the second component is attachable to a surgical extraction instrument. In addition, the device has a different coupling structure for driving attachment of the components to a prosthetic. The coupling structure includes a groove 140 in the ball portion of the second component and a rod 142 which extends across the socket in the first component. By pushing the second component downwards, the second component slides within the socket of the first component such that the groove engages the rod in the socket. The components are then locked together such that rotation of the second component, e.g. via a surgical extraction instrument, causes rotation of the first component to attach the first component to the prosthetic. After connection to the prosthetic, the second component can then be pulled upwards to disengage the groove and rod in an extraction configuration when transferring extraction forces to enable removal of the prosthetic component from the patient. In other respects the first and second components are similar in construction to those previously discussed. In particular, the first component has a socket and neck portion to retain the ball portion within the socket of the first component during extraction while enabling the components to be articulated.

Figure 14:
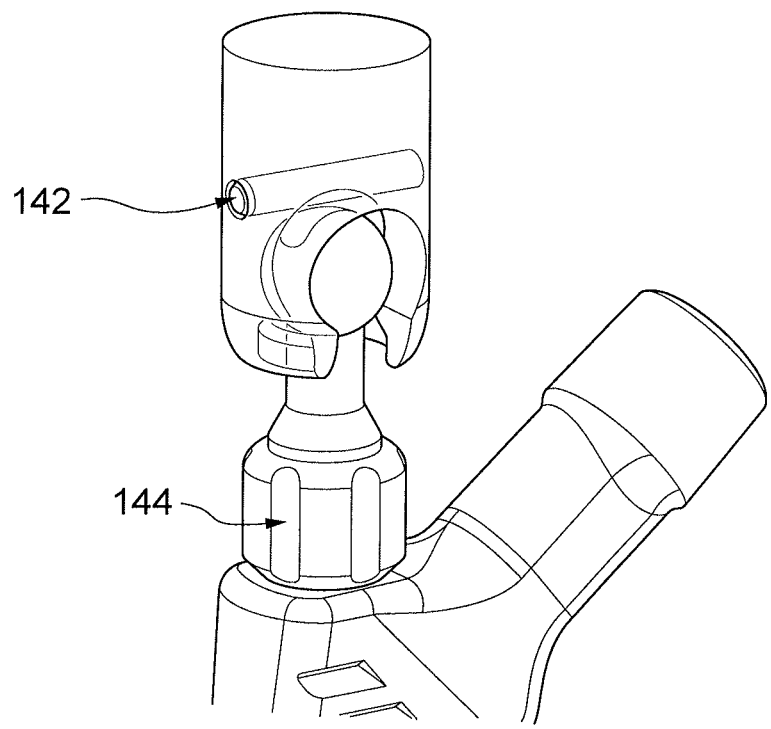
FIG. 14 shows another device for extraction of a prosthetic component from a patient, the device having a similar groove and rod coupling to the device of FIGS. 11 to 13 but with the order of the components reversed such that the second component is attached to the prosthetic and the first component is attachable to an extraction instrument.
Figure 15:
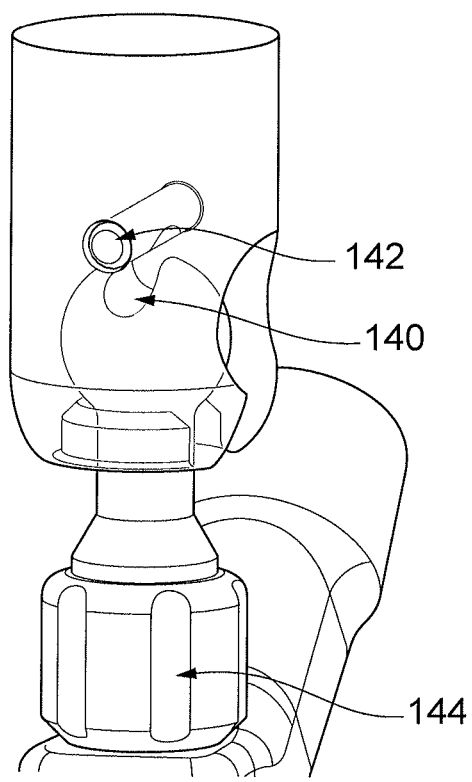
FIG. 15 shows another view of the device of FIG. 14.

FIGS. 14 and 15 show another device for extraction of a prosthetic component from a patient. The device has a similar groove 140 and rod 142 coupling to that of the device of FIGS. 11 to 13. The main difference is that order of the components is reversed such that the second component is attached to the prosthetic and the first component is attachable to an extraction instrument. The second component also has a finger screw 144 which can be used to manipulate the second component in addition to the groove and rod coupling.

Figure 16:
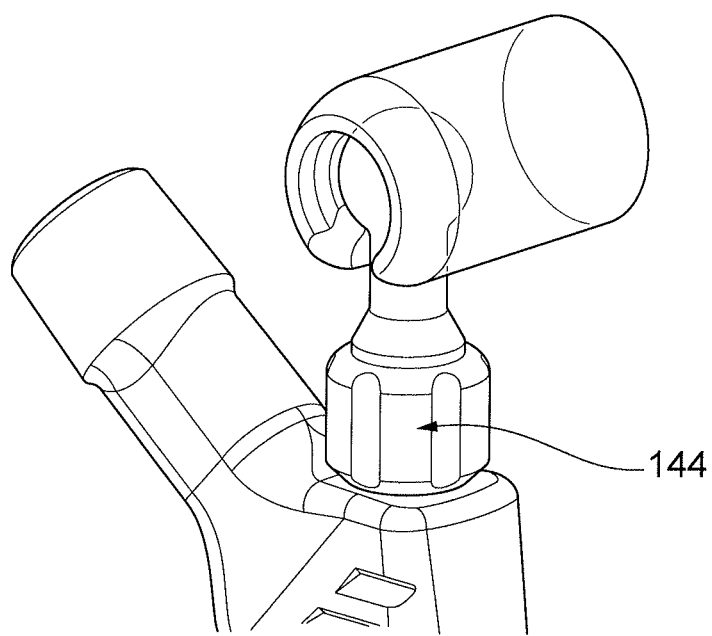
FIG. 16 shows another device for extraction of a prosthetic component from a patient, the device being configured to enable a large angular articulation of the first component relative to the second component.

FIG. 16 shows another device for extraction of a prosthetic component from a patient. The illustrated device comprises a finger screw 144 on the second component similar to the device of FIGS. 14 and 15. The first and second components are configured to enable a large angular articulation of the first component relative to the second component as illustrated in FIG. 16.

Figure 17:
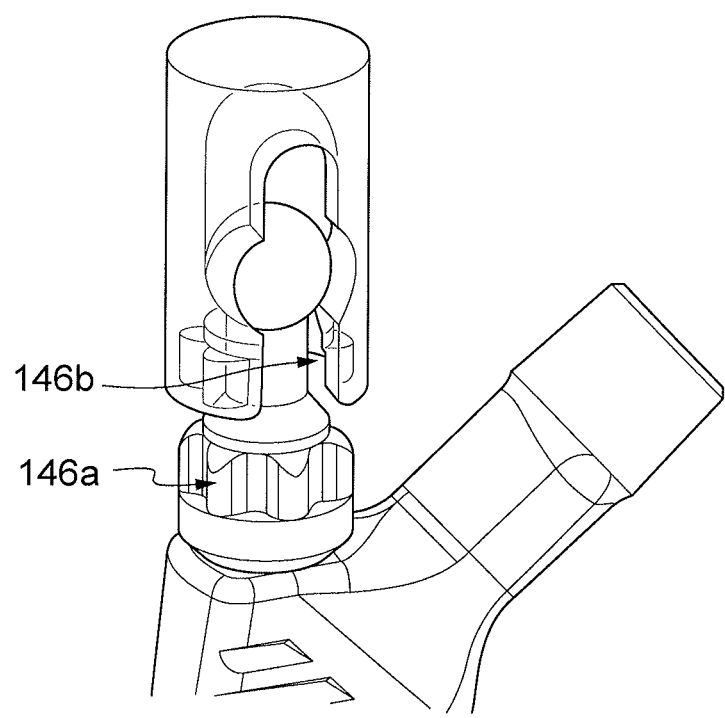
FIG. 17 shows another device for extraction of a prosthetic component from a patient, the device being similar in construction and function to the device shown in FIGS. 1 to 6 allowing the socket of the first component to be pushed down over the ball portion of the second component to engage a drive mechanism for attaching the second component to the prosthetic.

FIG. 17 shows another device for extraction of a prosthetic component from a patient, the device being similar in construction and function to the device shown in FIGS. 1 to 6 allowing the first component to be pushed down over the second component to engage a drive mechanism for attaching the second component to the prosthetic. In this case, a torx type drive is provided with complementary surfaces 146a, 146b on the second component and inner surface of the first component. Again, after attachment to a prosthetic, the first component can be pulled upwards sliding back over the second component in an opposite direction to disengage the drive connectors in an extraction configuration when transferring extraction forces to enable removal of the prosthetic component from the patient.

Figure 18:
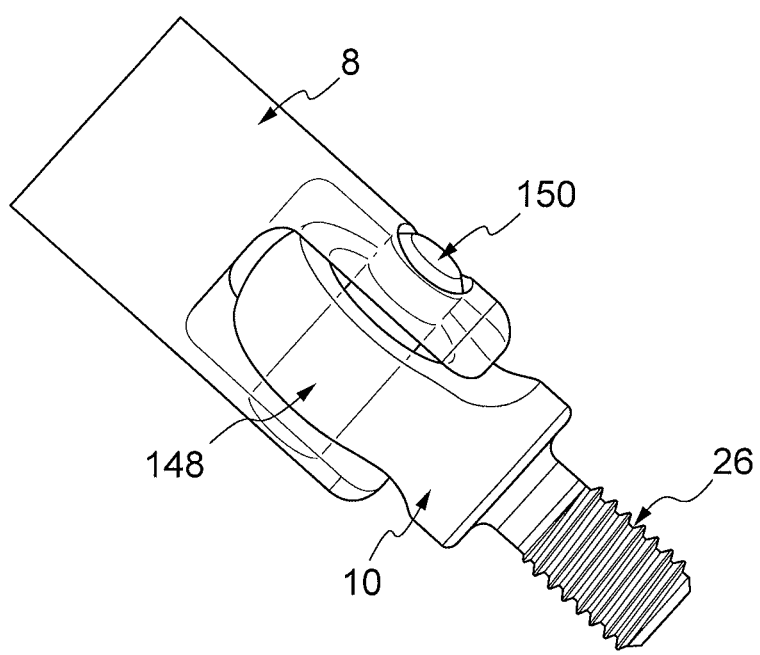
FIG. 18 shows another device for extraction of a prosthetic component from a patient, the device having a different coupling structure in the form of a ring and rod configuration.
Figure 19:
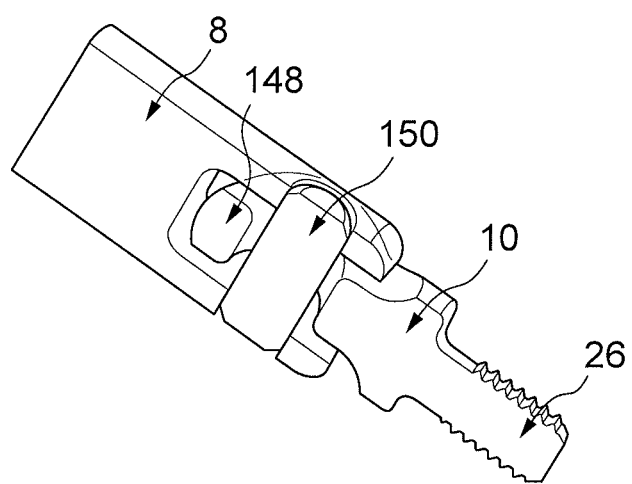
FIG. 19 shows a cross-sectional view of the device of FIG. 18.

FIGS. 18 and 19 show another device for extraction of a prosthetic component from a patient. The device comprises first and second components 8, 10 as in previous embodiments. The first component 8 has a female coupling portion in the form of a socket in which a portion of the second component 10 is disposed. The socket is defined by two arms extending from the second end of the first component so that the socket has an open end. The second component 10 has a male coupling portion, a stem, and an end connector 26 as in previous configurations. The device differs from the previously discussed configuration in that it has a different coupling structure in the form of a ring 148 and rod 150 configuration. The rod 150 extends across the socket in the first component 8. The male coupling component of the second component 10 comprises a ring 148, rather than a ball, which is disposed in the socket of the first component 8 with the rod 150 extending through the ring 148 to retain the second component 10 in the first component 8. When the first and second components are coupled together, the stem of the second component extends from the ring and out through the open end of the socket.

Figure 20:
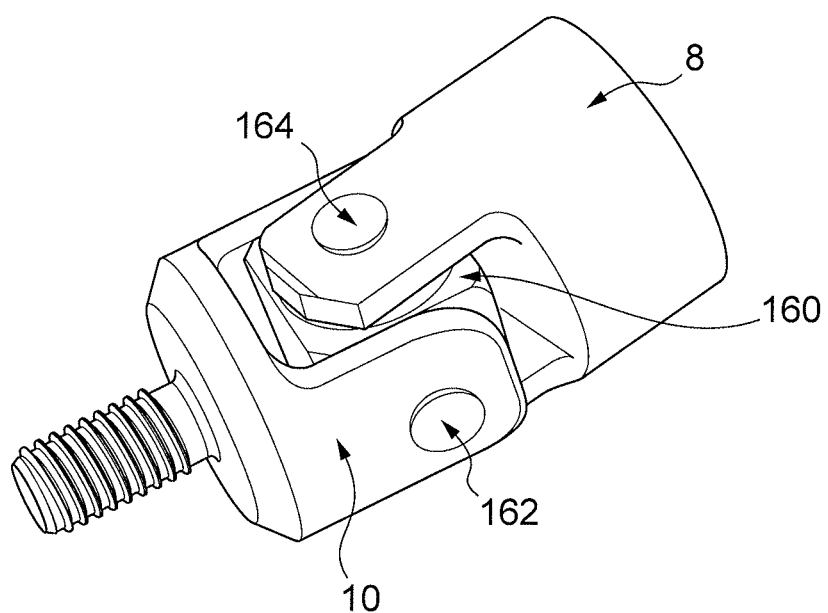
FIG. 20 shows another device for extraction of a prosthetic component from a patient, the device having a different coupling structure in the form of a universal joint configuration.

FIG. 20 shows another device for extraction of a prosthetic component from a patient, the device having a different coupling structure. The male coupling portion of the second component 10 is in the form of a rotatable member 160 mounted in the second component 10 on a first rod 162 for rotation around a first axis. The rotatable member 160 is disposed within the socket of the first component 8, and the retainer of the first component 8 is in the form of a second rod 164 oriented such that the rotatable member 160 is rotatable around a second axis perpendicular to the first axis, the first and second components 8, 10 thus forming a universal joint.

There are several ways in which the prosthesis extraction system as described herein can be constructed and used. For example, the first and second components (e.g. the ball and socket components) of the articulating joint can be pre-assembled prior to attachment to an extractor instrument and connected to a prosthetic component within a patient for extraction. Alternatively, one of the first and second components (e.g. the ball component) can be attached to the prosthetic within a patient and the other of the first and second components (e.g. the socket component) can then be coupled to the second component within the surgical site (e.g. via an opening in the first component) prior to extraction of the prosthetic component. Alternatively still, the prosthetic component can be provided with one of the first and second components already attached. For example, for ball and socket configurations as described herein, the second component of the joint can be pre-assembled to the prosthetic (although this could be the first component in other configurations). The second component attached to the prosthetic component can then be used to interface with an inserter to insert the prosthetic component as well as functioning as an interface with an extractor to extract the prosthetic component.

The disclosure also provides surgical devices having features specified in the following numbered clauses:

Clause 1: A surgical device for extraction of a prosthetic component from a patient during surgery, the surgical device comprising:

a first component having a side wall defining a cavity in the first component, a first end defining an open end, and a second end comprising a connector configured to be attached to one of a prosthetic component or a surgical extraction instrument, the first component further including a retainer; and a second component having a first end defining a coupling portion, a stem extending from the coupling portion, and a second end comprising an end connector configured to be attached to the other of the prosthetic component or the surgical extraction instrument, at least one of the first component and the second component further comprising a driver component for driving attachment of the said component to the prosthetic component, wherein the coupling portion of the second component is configured to be disposed within the cavity of the first component and retained within the cavity by the retainer with the stem of the second component extending from the open end of the first component, the coupling portion of the second component and the retainer of the first component being configured such that the coupling portion is held in the cavity while allowing articulation of the first component relative to the second component, the first and second components forming an articulating joint allowing a user to connect the surgical extraction instrument to the prosthetic component in a patient, articulate a portion of the surgical extraction instrument which resides external from the operating site, and transfer extraction forces to enable removal of the prosthetic component from the patient.

Clause 2: A surgical device according to clause 1,
wherein one of the first component and the second component is permanently attached to the surgical extraction instrument or removably attachable to the surgical extraction instrument.

Clause 3: A surgical device according to clause 1 or 2,
wherein the first component is configured to be attached to the surgical extraction instrument and the second component is configured to be attached to the prosthetic component.

Clause 4: A surgical device according to any preceding clause,
wherein the first component is a socket component and the second component is a ball component, and wherein the coupling portion of the ball component is a ball portion which is disposed within the cavity of the socket component, the retainer of the socket component being a neck portion disposed between the cavity and the open end of the socket component defining a narrow internal width compared to a width of the cavity, wherein the ball portion is configured to be disposed within the cavity of the socket component with the stem of the ball component extending through the neck portion and out through the open end of the socket component, the ball portion having a width which is larger than the width of the neck portion such that the ball portion is held in the cavity and prevented from passing out through the neck portion and open end of the socket component while allowing relative articulation of the ball and socket components, the ball and socket components thus forming a ball and socket joint.

Clause 5: A surgical device according to clause 4,
wherein the socket component comprises an opening in the side wall thereof, the opening having a complementary shape to that of the ball component to enable the ball component to be coupled and uncoupled from the socket component.

Clause 6: A surgical device according to clause 4 or 5,
wherein the opening in the side wall of the socket component is located such that when applying extraction forces to enable removal of the prosthetic component from the patient in use, the ball portion of the ball component cannot slide sideways out the opening in the side wall.

Clause 7: A surgical device according to any one of clauses 4 to 6,
wherein the driver component includes a drive connector disposed on the ball component between the stem and the end connector, the drive connector defining a surface for gripping and rotating the ball component to attach and release the ball component from the prosthetic component.

Clause 8: A surgical device according to clause 7,
wherein the socket component also includes a drive connector disposed on an internal surface of the side wall between the neck portion and the open end of the socket component, the drive connector of the socket component having a surface which is complementary to the drive connector on the ball component, wherein the socket component is configured to slide over the ball component to engage the drive connectors to enable the ball component to be driven to connect the ball component to the prosthetic component in an attachment configuration, the socket component being configured to slide back over the ball component in an opposite direction to disengage the drive connectors in an extraction configuration when transferring extraction forces to enable removal of the prosthetic component from the patient.

Clause 9: A surgical device according to clause 8,
wherein the drive connectors on the socket component and the ball component comprise complementary splines.

Clause 10: A surgical device according to any one of clauses 4 to 8,
wherein the drive connector on the ball component is a hex connector.

Clause 11: A surgical device according to any one of clauses 4 to 10,
wherein the ball portion of the ball component further comprises a drive component for driving attachment of the ball component to the prosthetic component.

Clause 12: A surgical device according to clause 11,
wherein said drive component is a hex drive.

Clause 13: A surgical device according to any one of clauses 4 to 12,
wherein the end connector of the ball component comprises a threaded connector with an unthreaded end portion.

Clause 14: A surgical device according to any one of clauses 4 to 7,
wherein the ball portion comprises a cavity and the socket component comprises a complementary projection, wherein the socket component is configured to slide over the ball component to engage the projection with the cavity to enable the components to be driven to connect the components to the prosthetic component in an attachment configuration, the socket component being configured to slide back over the ball component in an opposite direction to disengage the projection and cavity in an extraction configuration when transferring extraction forces to enable removal of the prosthetic component from the patient.

Clause 15: A surgical device according to clause 14,
wherein the projection is in the form of a rod and the cavity is in the form of a groove in the ball portion.

Clause 16: A surgical device according to any one of clauses 1 to 3,
wherein the coupling portion of the second component is in the form of a ring and the retainer of the first component is in the form of a rod which extends through the ring of the second component to couple the first and second components together while allowing articulation of the first component relative to the second component.

Clause 17: A surgical device according to any one of clauses 1 to 3,
wherein the coupling portion of the second component is in the form of a rotatable member mounted in the second component on a rod for rotation around a first axis, the rotatable member being disposed within the cavity of the first component, and the retainer of the first component is in the form of another rod oriented such that the rotatable member is rotatable around a second axis perpendicular to the first axis, the first and second components thus forming a universal joint.

Clause 18: A surgical system comprising:
 the surgical device according to any preceding clause; and
 a surgical extraction instrument configured to couple to one of the first component or the second component.

Clause 19: A surgical system according to clause 18, wherein the surgical extraction instrument is a slide hammer.

Clause 20: A surgical system according to clause 18 or 19, further comprising a prosthetic component configured to couple to the other of the first component and the second component.

Clause 21: A surgical system according to clause 20, wherein the prosthetic component is a femoral stem.

Clause 22: A surgical system according to any one of clauses 18 to 21, wherein the surgical extraction instrument is configured to couple to the first component and the prosthetic component is configured to couple to the second component.

Clause 23: A method of extracting a prosthetic component from a patient during surgery using the surgical system according to any one of clauses 18 to 22, the method comprising:
 coupling together the surgical device, the surgical extraction instrument, and the prosthetic component; and
 extracting the prosthetic component by applying an extraction force to the surgical extraction instrument.

While this disclosure has been described above in relation to certain embodiments it will be appreciated that various alternative embodiments can be provided without departing from the scope of the disclosure which is defined by the appending claims.

The invention claimed is:

1. A surgical device for extraction of a prosthetic component from a patient during surgery, the surgical device comprising:
 a first component having a female coupling portion at a first end, and a second end configured to be connected to one of a prosthetic component or a surgical extraction instrument, the first component further including a retainer; and
 a second component having a first end defining a male coupling portion, a stem extending from the male coupling portion, and a second end configured to be connected to the other of the prosthetic component or the surgical extraction instrument,
 wherein the male coupling portion of the second component is configured to be disposed within the female coupling portion of the first component and retained within the female coupling portion by the retainer with the stem of the second component extending away from the female coupling portion of the first component, the male coupling portion of the second component and the retainer of the first component being configured such that the male coupling portion is held in the female coupling portion while allowing articulation of the first component relative to the second component,
 wherein the female coupling portion is a socket and the male coupling portion is a ball portion which is configured to be disposed within the socket, the socket having a closed end and an open end, and the retainer of the first component being a neck portion of the socket disposed between the closed end and the open end of the socket and defining a narrow internal width compared to a width of the closed end of the socket,
 wherein the ball portion is configured to be disposed within the socket with the stem of the second component extending through the neck portion and out through the open end of the socket, the ball portion having a width which is larger than the width of the neck portion such that the ball portion is held in the closed end of the socket and prevented from passing out through the neck portion and open end of the socket while allowing relative articulation of the ball portion and socket, the ball portion and socket thus forming a ball and socket joint,
 the first and second components forming an articulating joint allowing a user to connect the surgical extraction instrument to the prosthetic component in a patient, articulate a portion of the surgical extraction instrument which resides external from the operating site, and transfer extraction forces to enable removal of the prosthetic component from the patient.

2. The surgical device according to claim 1, wherein at least one of the first component and the second component further comprises a driver component for driving attachment of the said component to the prosthetic component.

3. The surgical device according to claim 2, wherein the driver component includes a drive connector disposed on the second component between the stem and the second end, the drive connector defining a surface for gripping and rotating the second component to attach and release the second component from the prosthetic component.

4. The surgical device according to claim 3, wherein the drive connector on the second component is a hex connector.

5. The surgical device according to claim 1, wherein one of the first component and the second component is permanently attached to the surgical extraction instrument.

6. The surgical device according to claim 1, wherein the first component is configured to be attached to the surgical extraction instrument and the second component is configured to be attached to the prosthetic component.

7. The surgical device according to claim 1, wherein the socket comprises an opening in a side wall thereof, the opening having a complementary shape to that of the ball portion to enable the ball portion to be coupled and uncoupled from the socket.

8. The surgical device according to claim 7, wherein the opening in the side wall of the socket is located such that when applying extraction forces to enable removal of the prosthetic component from the patient in use, the ball portion cannot slide sideways out of the opening in the side wall.

9. The surgical device according to claim 1, wherein the ball portion of the second component further comprises a drive component for driving attachment of the second component to the prosthetic component.

10. The surgical device according to claim 1, wherein the ball portion comprises a cavity and the socket comprises a complementary projection, wherein the first component is configured to slide over the second component to engage the projection with the cavity to enable the components to be driven to connect the components to the prosthetic component in an attachment configuration, the first component being configured to slide back over the second component in an opposite direction to disengage the projection and cavity in an extraction configuration when transferring extraction forces to enable removal of the prosthetic component from the patient.

11. The surgical device according to claim 1, wherein an end connector on the second end of the second component comprises a threaded connector with an unthreaded end portion.

* * * * *